United States Patent [19]

McNall

[11] 3,955,282

[45] May 11, 1976

[54] PROCESS OF MOUNTING ORTHODONTIC BRACKET TO TOOTH

[76] Inventor: Earl G. McNall, 1510 El Monte Ave., Arcadia, Calif. 91006

[22] Filed: Mar. 3, 1975

[21] Appl. No.: 554,870

[52] U.S. Cl. .............................................. 32/14 C
[51] Int. Cl.² ........................................ A61C 7/00
[58] Field of Search ......................... 32/14 A, 14 C

[56] References Cited
UNITED STATES PATENTS

| | | | |
|---|---|---|---|
| 3,250,003 | 5/1966 | Collito | 32/14 A |
| 3,745,653 | 7/1973 | Cohl | 32/14 A |
| 3,797,115 | 3/1974 | Silverman | 32/14 A |

*Primary Examiner*—Robert Peshock

[57] ABSTRACT

An orthodontic method, dental composition, and apparatus are provided which permit the direct bonding of orthodontic brackets to teeth. In particular, a method has been devised whereby the tooth, following phosphoric acid etching, is treated sequentially with a primer, and a sealant which contains a catalyst, and a pre-mixed dental adhesive which permits the attachment of orthodontic brackets to teeth. More particularly, this invention permits the direct bonding of stainless steel attachments to teeth taking advantage of a low profile in the design of the bracket base method of attaching the bracket to the tooth which is curved to fit the individual tooth. Virtually any type of bracket may be welded onto this base and orthodontic treatment can proceed with greater patient comfort and convenience.

5 Claims, No Drawings

PROCESS OF MOUNTING ORTHODONTIC BRACKET TO TOOTH

BACKGROUND OF THE INVENTION

The conventional orthodontic appliances consist of an orthodontic band which is totally circumposed about every tooth and a bracket which is usually affixed by welding. The typical, present-day use of such apparatus requires the orthodontist to invest in a very large inventory of bands which are of proper anatomical design and size to fit every tooth. It is not unusual to require as many as 30 separate band sized for each type of tooth in order to obtain this desired aim. Furthermore, the ability of the orthodontist to correctly band the tooth depends upon his adhesive bonding of this band and its remaining in place throughout the entire treatment period without failure or without dental caries occurring under the band. It is further present-day practice to have the brackets prewelded to the bands and, of course, this increases the inventory of the orthodontist.

In the recent past, a variety of techniques have evolved for directly attaching orthodontic brackets to the surface of teeth. Of the methods in use, the first type utilizes orthodontic brackets molded from thermoplastics such as polycarbonate. These brackets are directly bonded to the surface of the teeth by means of an adhesive system which usually consists of a powder composed of an acrylate or methacrylate polymer and benzoyl peroxide, and a liquid monomer.

Each of these types of adhesives in use today require the mixing of this powder and liquid this is usually accomplished by means of a scoop for measuring the powder and an eyedropper for dispensing the liquid. This mixture is mixed with a spatula for a specific time period. These means of measurement are very crude and it is very difficult to control the time and uniformity of the mixing to provide optimum strength. Furthermore, in the bonding of each bracket, it is necessary to mix another batch of powder and liquid. The sources of error from this type of procedure are obvious since with a large excess of powder and insufficient liquid, there is a decrease in the strength from that of the optimum mix and the same is true if there is an excess of liquid over powder.

In addition, it may be noted that the time in which the adhesive polymerizes is a function of how much powder is used in the mixture. A further complication of this type of adhesive is that it must be sufficiently fluid that it will adequately wet the enamel rods of the enamel surface. When the mixture is sufficiently fluid to obtain this goal, the bracket containing the adhesive must be held in place for between one and two minutes until sufficient strength has been obtained to assure that the bracket will remain where it was positioned.

A further deficiency of this system is that polycarbonate brackets are insufficiently strong to withstand the intra-oral forces. Furthermore, the brackets are notoriously prone to creep under the load and they become scratched and discolored after a few months in use. This problem is particularly apparent with Edgewise techniques since an important requirement is to maintain an accurate rectangular slot throughout treatment and this is impossible with these brackets since they deform so much that the dimensional characteristics of the rectangular slot are degraded within a matter of a few days.

A variety of techniques have been described and are in use in direct bonding stainless steel brackets to teeth. These all depend upon mechanical interlocking of the bracket to the tooth. Examples include brackets welded to wire mesh through which the adhesive permeates, bracket bases with holes around the perimeter or throughout the bracket base through which the adhesive must be extruded, or box-shaped devices into which the adhesive must be placed and enclosed and mechanically interlocked.

The principal deficiency of wire mesh is that it must be of sufficient size to have strength on the weldments, otherwise they lack the strength required for orthodontic treatment. A further deficiency is that the wire mesh is unsightly and must be covered by the adhesive and since the adhesive mesh interface is rough, it serves as a site where cariogenic bacteria and food debris can accumulate. The bracket bases with holes around the periphery or throughout the entire base are only attached by the adhesive extruded through these holes. All that is required for failure of the bond is for mastication forces to shear the adhesive rods penetrating these holes. This comprises only a small fraction of the total area of the bracket base and, therefore, such bases have less strength than a base would have should all of the surface of the base be participating in bonding strength. In order for this type of bracket base to be cosmetically acceptable, it is necessary to feather out the adhesive which is extruded through these holes to form a surface which will cover what would otherwise be an unsightly area. This is a very time-consuming process. This type of bracket has a higher profile on the tooth and has higher torque forces in mastication.

An additional technique for direct bonding brackets to teeth consists of utilizing ultra violet light as a catalyst. In this type of system, polycarbonate brackets have been used extensively and recently this method has been applied to metal brackets which have bases with holes around the periphery. The major deficiency with this system is that it is necessary to hold an ultra violet light within 1 to 2 milimeters of the bracket and move it around the entire periphery of the bracket throughout the process of catalysis. This requires between one and two minutes for each bracket. Again, this process is time consuming and may even be dangerous, since there is insufficient history of the effects of ultra violet light on the viable tissues of the mouth.

One of the major causes of concern during orthodontic treatment is decalcification under the bands or brackets. The presence of wires and orthodontic appliances tend to entrap food debris, cariogenic bacteria thrive, and it requires diligence on the part of the patient in oral hygiene to prevent dental caries. Frequently beneath the brackets and bands this decalcification can take place and not be noticed until orthodontic treatment is completed and upon removal of the devices, such decalcification can be discovered. This is, of course, catastrophic. A method of preventing this has been in use in which a sealant is catalyzed by the ultra violet light previously described for the direct bonding of orthodontic brackets. The deficiencies of catalyzing the sealant with ultra violet light have been previously noted. Other types of sealants are in use for this purpose which unfortunately do not set up effectively because they are inhibited by air.

BRIEF SUMMARY OF THE INVENTION

This invention is directed to an improved method for direct bonding orthodontic brackets to teeth. This system consists of orthodontic brackets which are welded to stainless steel bases which have been chemically treated and curved in both the mesial-distal and gingival-occlusal planes to closely match the anatomy of the tooth. The surface of this bracket which faces the tooth is chemically treated to provide an enduring bond between the stainless steel and still not increase the bracket height on the surface of the tooth.

It is also an object of this invention to provide a sealant which can be painted onto the surface of the etched and primed tooth which does not require catalysis to form a polymeric barrier to the acids created by cariogenic bacteria. The sealant dries rapidly and provides the catalyst for the adhesive within the barrier film. This sealant can not only resist the effects of mouth acids, but can resist concentrated phosphoric, 50% sulfuric acid, and other strong acids for hours. The sealant may also be applied to the surface of the bracked base to aid in catalysis of the adhesive mass between the tooth and the bracket. In addition, the sealant is a resilient composition which increases the peel strength of this bonding system.

Additionally, since the linear coefficients of expansion of stainless steel, enamel, and the adhesive may be quite different, it is useful to have a resilient bond since such resilience permits large mismatches of linear coefficients of expansion without fear of degrading the strength of the adhesive bond. This latter characteristic provides much greater strength to the adhesive bond in situations where thermocycling is taking place; since the mouth is constantly thermocycling during the process of eating cold and hot foods and drinks, this is a very important characteristic which contributes to the reliability of the bonding system.

Another aspect of this invention is the adhesive itself. The adhesive is designed to be resilient and yet reasonable hard, sufficiently so to withstand the compaction of food on the interface of the adhesive joint and at the same time to diminish the strain produced by sudden shocks transmitted to the adhesive joint in the process of chewing. Furthermore, this adhesive is premixed and may be directly applied by using a spatula, or it may be expressed directly onto the bracket base by a syringe or similar device.

It is of great importance that the tooth following the etching stage be maintained in as dry a state as is possible to obtain constant patient comfort. In order to achieve this, the present invention includes a drying agent which causes the surface moisture to disappear and thereby provides an ideal surface for the bonding to occur.

A primer solution is described in this invention which is applied to the etched surface following the application of the drying agent. This primer serves to chemically link the tooth enamel with the sealant by means of a grafting reaction with the monomeric silane contained in the primer.

DETAILED DESCRIPTION OF THE EMBODIMENT OF THE INVENTION

In the practice of this invention the bottom of the bracket base is coated with bracket base coating. The tooth surface is etched with etching gel, coated with a safe dry composition, and then with a primer. Then both the bracket and tooth are coated with a sealant. Finally the bracket is coated with adhesive and promptly applied to the prepared tooth surface.

The bracket is pre-prepared with bracket base coating. The remaining steps are conducted by the orthodontist at the time of mounting of the bracket to the patient's tooth.

The bracket bases in this invention are produced from stainless steel strip material and may be as thin as that utilized in orthodontic bands (between 3 and 10 thousands inch thickness). The under surface of these formed structures is subjected to grit blasting to provide a surface of sufficient roughness. The roughness that is ideal for this purpose is on the order of 60 microinches or greater. Suitable standards have been developed to reproduce this degree of roughness.

Bracket Base Coating — The surface of the bracket is cleansed with trichlorethylene bath and is subsequently washed with methylene chloride, dried and sprayed with a solution of bracket base coating. This bracket base coating is applied in layers from the solution and after each layer has been sprayed, it is permitted to desolvate under an infrared lamp until the solvent has been removed and the process of spraying and desolvating is repeated until the bracket coat is of the desired thickness. The optimal thickness is between 1 and 3 milimeters.

Alternatively, it is possible to apply this coating by powder coating techniques. To prepare the powder, the polymer is melted, thoroughly mixed with the additives under high shear, extruded, cut and ground to approximately 150 mesh size.

Irrespective of which method is used to coat the base, it must be subsequently heated to the glass transition temperature or above to permit adequate bonding of this coating to the blasted surface of the stainless steel.

The most important limitation of the upper limit of the temperature used is the thermodegradation of the polymer itself which will cause a decrease in bonding strength. A second type of undesirable effect is the change in color of the stainless steel attachment and base if the temperature is excessive.

The following are a series of examples of spray-type coatings for the bracket bases.

Suitable polysulfones which can be employed in accordance with the present invention include extrusion grades of polysulfones and injection molding grades of polysulfones such as those having molecular weights of 3500 to 1600, and presently manufactured by Union Carbide, designated as P-3500 and P-1600.

Alternatively or additionally, polyethersulfones may be utilized. The sulfones are dissolved in a suitable solvent of which 1 methyl, 2 pyrrolidinone is the most practical. Dimethyl formamide and/or chlorinated solvents may also be used. However, additional care must be taken in the desolvation steps since it is often difficult to remove these solvents from the coating. Examples of chlorinated solvents are methylene chloride and trichloroethylene.

Mixtures of these various solvents may also be utilized. The optimum concentration of polymer in solvents is approximately 22.5%. However, satisfactory concentrations can range as low as 10% and as high as 30%. This bracket base coating may be reinforced and ideally, the reinforcement fiber is a titanium dioxide fiber designated as Fybex E manufactured by DuPont Corporation. Other fibrous types of reinforcement are also effective if they are compatible and can be adequately dispersed in the mixture. For these fibers to be most effectively incorporated, they must be coated with one of the following types of treatments:

Vinyl dimethyl chlorosilane, viny dimethyl methoxysilane, divinyl chloromethoxy silane, vinyl trichlorosilane, vinyl dichloromethylsilane, 3-(trimethoxysilane) propyl methacrylate, or cinnamate, 3-(glycidoxy propyl) trimethoxysilane, bis (glycidoxy propyl) dimethyl disiloxane, trimethoxy vinyl silane, triethoxy vinyl silane, vinyl silyl triacetate and diallyl diethoxy silane.

It should be pointed out, however, that any or all of the above, or equivalent silane bonding agents, may be advantageously utilized in accordance with the present invention as a substantially monomolecular coating upon the fiber particles to improve the adhesion between the filler and the resin component of this novel orthodontic composition. It is often desirable in accordance with this invention to include within the composition as a minor component a submicron thickener such as submicron silica to aid in controlling the viscosity when the lower regions of concentration of this polymer are utilized.

An additional component may be added to the system which consists of a yellow or brown oxide of iron, commonly used as pigments. Such examples are yellow powdered iron oxide, designated as Y05087 from William's Colors and Pigments, Pfizer Minerals and Pigments. The purpose of this yellow or brown additive is to serve as a visual indicator that the bracket base coating has been adequately baked in the post-cure stage. A concentration of 0.01% is as barely perceptible and is most useful in concentrations of 0.05% and higher.

Upon baking at a temperature approximately the glass transition temperature or higher, the iron oxide interacts with the polymer to create a reddish hue which is easily distinguished from the previous yellow or brown color. This provides a visual evidence that the bracket base coating has been adequately cured. Other iron oxides may be substituted for this purpose as long as they fulfill the previously described requirements.

Example No. 1 — Polysulfone P-3500 is dissolved in 1 methyl, 2 pyrrolidinone to a concentration of 22.5%. Silane treated Fybex E is added to a concentration of 2% and yellow iron oxide, finely powdered, is added to a concentration of 0.05% and the mixture is continuously mixed in a high-speed blender (for example a Waring blender) for fifteen minutes or until the mixture is completely homogenous.

Example No. 2 — Polysulfone P-3500 is dissolved in dimethylformamide to a concentration of 22.5%. Silane treated Fybex E is added to a concentration of 2% and yellow iron oxide, finely powdered, is added to a concentration of 0.05% and the mixture is continuously mixed in a high-speed blender (for example a Waring blender) for fifteen minutes or until the mixture is completely homogenous.

Example No. 3 — Polysulfone P-3500 is dissolved in trichloroethylene to a concentration of 2% and yellow iron oxide, finely powdered, is added to a concentration of 0.05% and the mixture is continuously mixed in a high-speed blender (for example a Waring blender) for 15 minutes or until the mixture is completely homogenous.

Following the spraying steps and desolvation under the infrared lamp in a hood, it is necessary to conduct a post cure of this coating at 550°F. The basic requirements at this stage are that the coating be as completely desolvated as possible before the final heat cure and that the heat cure, if it is conducted in the presence of oxygen, be as brief as possible consistent with the adequate bonding of the coating to the metal backing. Prolonged heating at 550° F in air leads to the formation of a brownish discoloration on the surface of the stainless steel bracket and this is undesirable.

Additionally, some degradation of the polymer interface with the metal takes place resulting in a weaker bond. This post-cure heat treatment can also be accomplished in an oven equipped to be purged by an inert gas such as nitrogen, argon, helium, etc. This results in very little degradation of the polymer and does not cause staining of the stainless steel.

The polysulfone, or polyethersulfone, may be melted and the reinforcing fibers added to the melted polymer in the same proportions as were previously discussed in the liquid phase coating.

Following this melt, and adequate mixing of the fibers in the melt, the object is to reduce the polymer fiber mixture to fine particles between 100 mesh and 400 mesh. The ideal mesh size is between 150 and 250 mesh simply because commercial equipment is designed to utilize mesh of this size in powdered coatings. The powdered coating may be sprayed onto the backs of the brackets using powder coating techniques and the curing is accomplished at the temperatures previously discussed.

Example No. 1 — Polysulfone 3500 - 100 grams, Silane treated Fybex E — 5 grams and, in this case, it is not useful to utilize the iron oxide since it would change color in the polymer melt.

Following this melting procedure and mixing, the material may be extruded and cut into pellet size, similar to that of thermoplastics and subsequently powdered by one of the various types of powdering techniques known in the powder coating field.

For the other examples of powder coatings of polysulfone, make example No. 2 the same concentration of Fybex E, but substitute polysulfone P-1700 and example No. 2 would be the same concentration of Fybex E, but substitute polyethersulfone.

Etching Gel

The etch solution utilized in this invention is composed of phosphoric acid in gel form. The optimal concentration is in the vicinity of 50%. Concentrations below 50% require longer time for effective etch on human enamel and there is no appreciable advantage to having higher concentrations of phosphoric acid beyond 50% since the etching process is not aggressively faster and there is an additional hazard because of the corrosive nature of this acid.

It is advantageous to include a dye in this gel to facilitate visual detection of its presence on the tooth. A suitable dye is amaranth red color No. 2. Suitable concentrations range from 0.001% to approximately 0.05%. To this 50% phosphoric acid solution containing amaranth, a finely divided silica is used as a thickening agent to transform the solution to a stable gel. A fumed, anhydrous particulate colloidal submicron silic which is satisfactory is Cabosil M-5, which is manufactured by Cabot Corporation. Useful concentrations of these thickening agents range between 5% and 12%, with the optimum at approximately 8%.

Orbond Safe Dry

The etching gel is then thoroughly rinsed from the tooth, which is thus readied for reception of the safe dry composition.

This preparation is used to remove the moisture from the surface of the etched enamel and consists of a mixture of several ingredients which perform specific functions. The first ingredient is a non-toxic or a low toxicity chlorinated hydrocarbon which is ideally non-flammable. Such a liquid is methylene chloride. Various of the freons may be utilized.

The purpose of this ingredient is to serve as a carrier of the more active materials for displacing water on the surface of the tooth, and it should volatilize quickly leaving the less volatile active ingredients present. While methylene chloride and certain of the other chlorinated and/or fluoridated hydrocarbons do remove moisture by themselves, they are less efficient than the mixtures to be described as our product Safe-Dry.

N-butyl alcohol is an ideal ingredient in this type of preparation since it is efficient in displacing moisture from the surface of the etched tooth, and it is also reasonably volatile. Ethyl alcohol is slightly more volatile then the n-butyl alcohol, but is less efficient than n-butyl alcohol in the removal of moisture. The ethyl alcohol is used in conjunction with the n-butyl alcohol to aid in the removal of the latter alcohol by coevaporation. A further advantage of the composition of ethyl alcohol and n-butyl alcohol in the methylene chloride is that while being volatile and effective in the removal of water, the overall composition is non-flammable. The ratio of ethyl alcohol to n-butyl alcohol is ideally on the order of 3 to 1. However, suitable and useful concentrations can range from 1 to 1, to 5 to 1.

Example No. 1 — 3.2 liters methylene chloride, 0.6 liters ethyl alcohol, 0.3 n-butyl alcohol.

Primer

The primer consists of a solvent which is volatile and non-reactive with the active ingredients in the primer. An example is methyl ethyl ketone. This solvent rapidly volatizes following its application on the dried enamel. It also serves to remove whatever residual moisture has escaped the safe-dry preparation treatment.

The active ingredient in the primer is triethoxy vinyl silane. This silane reacts with the enamel on the surface of the tooth to form a bond which is capable of reacting with the sealant and the migratory species of monomer from the adhesive. This results in a grafting process in which the enamel, sealant and adhesive are chemically interacted.

Examples of other silances which may be utilized are trimethoxy vinyl silane, trimethoxy ethoxy vinyl silane, gamma (methacryloxy propyl) tri methoxy silane, diallyl dioxy silane, 3-(methoxy dimethyl silyl) propyl allyl fumarate, and 3-(chlorodimethyl silyl) propyl methacrylate.

It is to be pointed out, however, that any or all of the above equivalent silane bonding agents may be advantageously utilized in accordance with the present invention. Useful concentrations of the silane range from 0.02% to approximately 1%, with the optimum concentration being approximately 0.4%. The solvent in these cases should not contain chlorinated hydrocarbons as they interact with the silanes and to be useful, the solvent should be quite volatile and yet easily handled. Methyl ethyl ketone, ehtyl alcohol and isopropyl alcohol are examples of suitable solvents to be used in this system.

Example No. 1 — Triethoxyvinylsilane 0.4% in ethyl methyl ketone.

Example No. 2 — Trimethoxyethoxyvinylsilane 0.4% in ethyl alcohol.

A feasible, but less satisfactory, process can be effected eliminating the safe-dry and/or the primer.

Sealant

The sealant is composed of a polymer or pre-polymer which has the capability of bonding or at least being compatible with the primer and the enamel of the tooth and interacting chemically with the adhesive. A further constituent is a free radical source such as benzoyl perioxide.

The sealant polymer should have as high a tensile strength as possible and be cross-linkable with the silane monomer used in the primer and the monomer present within the adhesive itself. Such monomers include a significant variety of acrylates and methylacrylates, the most useful of which are the methlacrylates. In addition to the preceding monomers, such monomers as styrene and alpha methyl styrene may be utilized. The monomer which produces the most crystaline type of material is mathylmethacrylate. The principal disadvantage of using this monomer alone is that it is quite inelastic and tends to not have maximal or optimal bonding characteristics to the enamel surface. The same is true of ethyl methylacrylate. On the other hand, as one increases the carbon chain to propyl, butyl, pentyl, cyclohexy, hexyl, nonyl, decyl, undecyl, dodecyl, etc., or the iso variety of these several monomers, the polymer film becomes more elastic,, has a higher resistance to peel, but unfortunately has an increase in softness.

For practical purposes, copolymers consisting of methylmethacrylates and a second higher methacrylate, preferably between butyl and octyl, may be copolmerized in various ratios. In order to increase the bonding strength between the enamel and the polymer film, it is useful to have a small percent (between 0.2% and 5%) of an acid moeity of an acrylate or methacrylate. There is a further advantage of having styrene moeities present because they increase the electron density and hence the bonding infinity between the polymer itself and the enamel interface. While this is not absolutely necessary, it does increase the strength of bonding between the various constituents which interact with the sealant.

It is, of course, advantageous to have such prepolymer or polymers used within the sealant to have end groups which are accessible to covalant bonding. Such end groups as methacrylates or acrylates are ideal. Allyl groups are much slower in reaction and require a much longer time period than would be ideal for use in the sealant.

It is possible to substitute some fraction of the longer chain acrylates with acrylonitrile. Homopolymers of acrylonitrile are quite elastic and rubberlike in quality and, in fact, are too rubbery to be practical for use as a sealant. Its use in conjunction with the harder, more crystaline polymer producing monomers, such as methylmethacrylate, does result in satisfactory compositions.

There is an additional series of monomers which are useful in conjunction with the aforementioned monomers and this includes such monomers as benzyl methacrylate, phenyl ethyl methacrylate, and similar types of monomers. The increased peel resistance of primers containing the latter types of monomers is due to the presence of pi electrons in the aromatic rings.

It should be noted, however, that the copolymer containing benzyl methacrylate have a higher peel strength than the one containing phenyl ethyl methylacrylate. It is likely that this difference is due to the increased aeromaticity of the benzyl group over the phenyl groups. Here again, homopolymers consisting only of these monomers are not practical because they lack tensile strength and therefore it is necessary that they be incorporated and substituted for the higher acrylates and be used in conjunction with methylmethacrylates in the formulation of satisfactory sealants.

Sealant examples include the following:
Example No. 1
  Butyl methacrylate — 10 to 30%
  Methyl acrylic acid — 0 to 8%
  Methylmethacrylate — the remainder
Example No. 2
  Styrene — 5 to 15%
  Methyl acrylic acid — 0 to 8%
  Methylmethacrylate — the remainder
Example No. 3
  Styrene — 0 to 15%
  Acrylonitrile — 5 to 30%
  Methylmethacrylate — the remainder Various combinations and substitutions of butyl methacrylate and higher acrylates may be made with the acrylonitrile. Concentrations of acrylic acid or methacrylic acid up to 8% may be included. The optimum concentration of this monomer is approximately 4%. Polymers prepared as previously described are soluble in a variety of solvents including the chlorinated hydrocarbons such as chloroform, methylene chloride and trichloroethylene. They are dissolvable in a variety of other solvents. The most useful composition of the sealant is benzoyl perioxide approximately 10%, (but effective concentrations range between 2% and 15%) and the polymer at a concentration which is ideally 15%. The most useful solvent discovered thus far is chloroform since the chloroform evaporates rapidly leaving a smooth film of the sealant on the surface of the primer-treated tooth. Within a few seconds of applying the sealant, the adhesive may be added when conditions are such that the rapid evaporation of the chloroform can take place.

Adhesive

The adhesive consists of the following constituents. The polymer backbone and an amine which interacts satisfactorily with the free radical generator present in the sealant, a mobile monomer such as methylmethacrylate, ethyl methacrylate, propylmethacrylate, etc., and small concentrations, if present at all, of dimethacrylate to cross-link the polymer in the process of polymerization.

It is also useful to use a polymer which is slightly compatible with the adhesive such as in this case, acrylonitrile butadiene styrene polymers. These may be included in various ratios depending upon the physical characteristic desired. Presence of the latter type of polymer increases the resistance of the adhesive bond to permanent deformation and/or fracture from the shock transmitted through mastication. Other components of the adhesive are anti-oxidants to trap free radicals present during the manufacture of adhesive or which may contaminate various of the ingredients present in the compounding of the adhesive itself. Such anti-oxidants as butylated hydroxy toluene (BHT) are useful. Other types of inhibitors include hydroquinone, catechol, catechol methyl ether, tert.-butyl catechol, purogallol, pyrogallol monomethylether, pyrogallol dimethyl ether. Of these, the most useful, as has been previously indicated, is the butylated hydroxy toluene, or BHT.

Additionally, it is necessary to store the adhesive when it is fully compounded in a bottle which is either dark or treated such that fluorescence from the glass itself will not create free radicals.

There is much greater range of utility of monomers in the adhesive than there is in the sealant. The adhesive can be formulated from methylmethacrylate prepolymer and methylmethacrylate monomer. However, its strength and, in particular, its peel strength, is quite low. This strength can be increased slightly be substituting cyclohexy acrylate or cyclohexyl methacrylate as a monomer and using powdered methylmethacrylate polymer. However, again this slight increase in peel strength is not sufficient to overcome the advantages of other adhesives which will be discussed later.

In particular, adhesives consisting of styrene, butyl methacrylate and methylmethacrylate are stronger and more resilient in their bond strength than the previous system. Systems including the former monomers but lacking styrene are also effective. It is possible also to utilize polymers which consist of various of the substitutes discussed previously in the section entitled "Sealant".

In all of these cases, it is not necessary to contain within the polymer acrylic or methacrylic acids since the bonding between the enamel is already accomplished with the aid of the sealant. In fact, the presence of acrylic or methacrylic acid slightly degrades the system since these moeities are hydrophylic. The following are examples of the composition of the adhesive polymer.

Example No. 1
  Styrene — 0 to 15%
  Butyle methacrylate or higher acrylate — 5 to 20%
  Methylmethacrylate — the remainder
Example No. 2
  Styrene — 0 to 15%
  Butyl methacrylate or higher acrylate — 5 to 20%
  Divinyl benzene — 0 to 1.5%
  Methylmethacrylate — the remainder
Example No. 3
  Butyl methacrylate or higher acrylate — 5 to 20%
  Methylmethacrylate — the remainder
Example No. 4
  Styrene — 0 to 15%
  Butyl methacrylate or higher acrylate — 5 to 20%
  Methylmethacrylate — the remainder
Example No. 5
  Styrene — 0 to 15%
  Acrylonitrile — 5 to 20%
  Methylmethacrylate — the remainder These polymers are dissolved in either methylmethacrylate or a mixture containing methyl methacrylate and other high acrylates. However, the optimum has to have at least a ratio of 3 to 1 of methyl methacrylate to other higher methacrylates.

The percentage of polymer to monomer is approximately 50%. The lower the concentration of the polymer and the higher the concentration of the monomer, the slower the reaction. When this 50-50 ratio is approximately achieved, it is useful to add 1-5% of a finely divided silicate such as Cabosil M-5 or more ideally, a silanated derivative of fumed silica. At a concentration between 1 and 5%, the polymer is sufficiently thickened to permit its adhesion upon the teeth upon contact. This adhesion still permits manipulation through a period between 20 seconds and 1 minute after contact with the sealant-covered tooth. Amine is added to a concentration of between 0.2% and 2%, to the adhesive mixture to increase the rate of reaction between the benzyl peroxide present within the sealant and the monomers present within the adhesive. Amines which are satisfactory for this purpose are N, N-dimethyl-p-toluidine, N,N-diethyl-p-toluidine, and 2,2'M-tolyldiethanolamine.

Whereas the present invention has been shown and described herein in what is conceived to be the best mode contemplated, it is recognized that departures may be made therefrom within the scope of the invention which is therefore not to be limited to the details disclosed herein, but is to be afforded the full scope of the invention.

What is claimed is:

1. Process of mounting an orthodontic bracket to a tooth, comprising the steps of:
   1. coating the bracket with a bracket base coating comprising polysulfone or polyether sulfone;
   2. etching the tooth surface with a gel comprising phosphoric acid and a thickening agent;
   3. applying to both tooth and bracket a sealant comprising a mixture of:
      a. a polymer or pre-polymer which is compatible with the tooth enamel and which chemically interacts with the adhesive (to follow), and
      b. benzoyl peroxide or derivatives thereof;
   4. coating the bracket with an adhesive comprising a mixture of:
      a. methyl and/or ethyl methacrylate, and
      b. monomers of butyl and higher acrylates and/or methacrylates;
   5. applying the bracket to the prepared tooth surface.

2. Process in accordance with claim 1, including additionally the step of drying the tooth, after etching, with a safe-dry composition consisting of:
   a. a low toxicity, volatile, chlorinated hydrocarbon, and
   b. an alcohol higher than ethyl.

3. Process in accordance with claim 1, including in addition the step of applying to the tooth, prior to coating with the sealant, a primer consisting of a silane monomer which is capable of bonding to the tooth enamel and is dissolved in a volatile, inert solvent.

4. Process in accordance with claim 1 wherein said sealant includes:
   c. an acidic monomer.

5. Process in accordance with claim 4 wherein said polymer or pre-polymer is resilient.

* * * * *